United States Patent [19]
Diamond

[11] Patent Number: 4,798,655
[45] Date of Patent: Jan. 17, 1989

[54] MULTIPARAMETER ANALYTICAL ELECTRODE STRUCTURE AND METHOD OF MEASUREMENT

[76] Inventor: Howard Diamond, 121 Huronview Blvd., Ann Arbor, Mich. 48103

[21] Appl. No.: 27,846

[22] Filed: Mar. 19, 1987

[51] Int. Cl.[4] .................... G01N 27/46; G01N 27/48; G01N 27/50
[52] U.S. Cl. ................... 204/1 T; 204/416; 204/431; 204/433
[58] Field of Search ............. 204/1 T, 1 Y, 1 K, 1 F, 204/1 H, 416, 431, 432, 433, 435

[56] References Cited

U.S. PATENT DOCUMENTS

| | | | |
|---|---|---|---|
| 2,913,386 | 11/1959 | Clark | 204/415 |
| 4,227,974 | 10/1980 | Petersen | 204/1 F |
| 4,452,672 | 6/1984 | Parker | 204/407 |
| 4,561,963 | 12/1985 | Owen | 204/433 |
| 4,563,263 | 1/1986 | Oyama | 204/433 |

FOREIGN PATENT DOCUMENTS

1193564-A  3/1984  U.S.S.R. .............. 204/1 Y

*Primary Examiner*—John F. Niebling
*Assistant Examiner*—Ben C. Hsing
*Attorney, Agent, or Firm*—Krass & Young

[57] ABSTRACT

An ion sensitive electrode device and method of its use in analytical and clinical chemistry are provided for measuring the concentration of an ionizable analyte contained in an aqueous medium. The device with external circuit means includes an electrode pair adapted to be placed in electrochemical contact with the medium. The electrode pair includes a polarographically active base metal/metal oxide working electrode and a reference electrode. The external circuit means is adapted to measure the voltage generated by the electrode pair in open circuit and to measure the closed circuit current flow at a preselected impedance and including means for comparing said voltage and current flow values with predetermined reference standards to provide a third value representative of said analyte concentration.

16 Claims, 1 Drawing Sheet

MULTIPARAMETER ANALYTICAL ELECTRODE STRUCTURE AND METHOD OF MEASUREMENT

DESCRIPTION

1. Technical Field

This invention relates to electrochemical apparatus and methods for sensing or measuring chemical ionic species as well as dissolved gases such as blood gas parameters in aqueous media, physiological media, and the like.

2. Background of the Invention

Measurement of gas pressures in aqueous fluids by polarography is conventional. Polarographic sensors are commonly used, for example, in the monitoring of the partial pressure of dissolved oxygen ($PO_2$) in blood. One common form of $PO_2$ sensor is based on a design described by L. C. Clark (e.g., see U.S. Pat. No. 2,913,386) and includes a noble metal cathode, a buffered electrolyte, and a reference electrode. Oxygen present in the electrolyte migrates to, and is electrochemically reduced at, the cathode. The magnitude of current flow resulting from an applied potential at the cathode is a measure of $PO_2$.

A more versatile apparatus for simultaneous $PO_2$ and partial pressure of carbon dioxide ($PCO_2$) sensing by polarography employing a single sensor that is an inert, noble metal surface is an apparatus described by Parker et al. in U.S. Pat. No. 4,452,672. The apparatus uses a reference electrode with the inert electrode, and one applies an external polarizing voltage to produce a current in the fluid sample between the electrodes. The electrode itself does not enter into a chemical reaction.

SUMMARY OF THE INVENTION

The present invention is based on the discovery of a novel type of base metal-metal oxide sensor that is sensitive both to dissolved gases such as oxygen as well as to ionized species such as $H^+$ (pH) and, in the presence of an electrolyte, exhibits a stable electrochemical potential difference with respect to a reference electrode. This potential is proportional to an ionic concentration parameter such as pH. In addition, the sensor acts as its own potential source so that an externally applied voltage is not necessary for current flow in the fluid sample. In this case, the electrode material is not chemically inert and in fact enters into a chemical reaction with the analyte. For example, for an antimony surface:

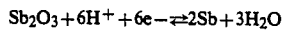

$$Sb_2O_3 + 6H^+ + 6e^- \rightleftharpoons 2Sb + 3H_2O$$

Here the equilibrium potential is a function of the hydrogen ion concentration (pH).

The invention in one aspect relates to an electrochemical method of measuring the concentration of a given ionizable analyte contained in an aqueous solution. The method employs an electrode pair including an active, pH-sensitive, base metal/metal oxide working electrode and a reference electrode. The working electrode is of a material which is also polarographically active (i.e., can be used in an amperometric mode) in the presence of the analyte to a degree which is a measure of the concentration of the analyte in the solution.

The method in a preferred embodiment comprises the steps of measuring the open circuit voltage generated by the electrode pair in contact with the aqueous medium, measuring a closed circuit current, which may be a short circuit current, and comparing said voltage and current values with predetermined reference standards to provide values of two parameters representative of said analyte concentrations. Thus, the method employs a combination of potentiometric and amperometric measurements, (say, to determine pH and $PO_2$ simultaneously or in rapid sequence). The measurements and reference comparison can conveniently be done by processing the derived signals in an electronic microprocessor.

In another preferred embodiment which is similar, the method comprises the steps of carrying out first and second measurements of the polarographic current at given first and second applied or driven steady-state voltages, respectively; and comparing the resulting observed first and second current values with predetermined reference standards to provide two values representative of concentrations of two dissolved gas analytes of interest for example, $PO_2$ and $PH_2$. Then, in addition, carrying out measurement of the open circuit potential and comparing the observed value provides a value indicative of concentration of an ionic species such as $H^+$ (pH). The methods of the invention, by selection of a suitable polarographic negative or positive driving potential are applicable to the measurement of any of various gas analytes such as oxygen, carbon dioxide, hydrogen, methane, hydrogen sulfide and the like.

The invention in another aspect relates to a combination potentiometric and polarographic electrode device for measuring the concentration of an ionizable analyte (such as pH) contained in an aqueous medium. The device, for use with external circuit means includes an electrode pair adapted to be placed in electrochemically sensing contact with the medium, the first electrode being a polarographically active base-metal/metal-oxide working electrode and the second being a reference electrode such as a silver/silver-chloride electrode or a calomel electrode. The external circuit means which may be conventional is adapted to measure the voltage generated by the electrode pair in open circuit and to measure a momentary closed circuit current (e.g., a pulse current for about 0.01 to 10 seconds) at a preselected impedance. The external circuit includes means for comparing said voltage and current values with predetermined reference standards to provide two values representative of concentration of the analyte of interest. Specific details concerning the device are set forth in the description which follows.

BRIEF DESCRIPTION OF THE DRAWINGS

Referring to the drawings annexed herewith.

DETAILED DESCRIPTION OF THE PREFERRED EMBODIMENT

Figure 1:
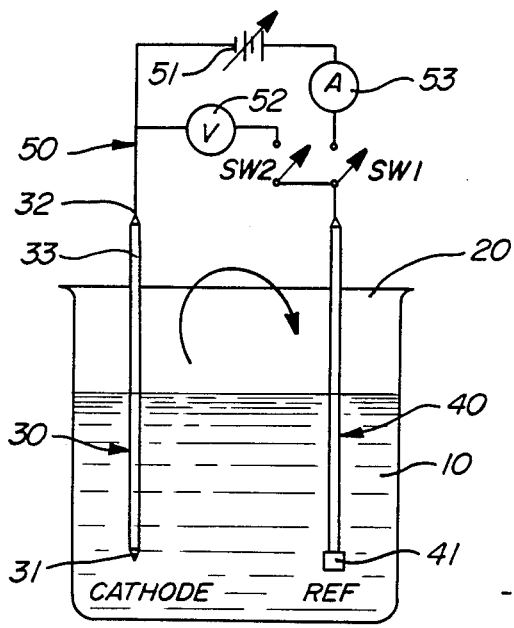
FIG. 1 is a diagrammatic view of a preferred embodiment of a measuring apparatus according to the invention.

Referring to FIG. 1, an aqueous fluid sample 10 containing dissolved gas (e.g., oxygen) is confined in a measuring chamber 20 which may be a flowthrough chamber. An active electrode 30 and a reference electrode 40 are disposed with their sensor ends 31,41 immersed in the fluid sample 10. The electrodes are connected by conductive lines 32,42 to an external circuit 50 including a voltage supply 51, voltmeter 52, ammeter 53, and switches $S_1$ and $S_2$. It is to be understood that switches $S_1$ and $S_2$ can be microelectronic switches in the external circuit. Similarly, the voltmeter and ammeter can be microelectronic measuring devices. The cathode 31 in a preferred form, comprises a chemically active metal surface, preferably an antimony surface, enclosed in a insulative glass or plastic sleeve 33 open at its tip so that a polarographic sensor small area of metal (e.g., antimony) is exposed which naturally develops a co-extensive, corresponding metal oxide layer (not shown). The reversible electrochemical reaction entered into with the ion being sensed is in the case of antimony given by the equation:

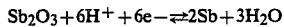

$$Sb_2O_3 + 6H^+ + 6e^- \rightleftharpoons 2Sb + 3H_2O$$

$E = E_o - 0.059\, pH$, with $E_o = 0.145$ volts for Sb relative to a standard hydrogen electrode.

The measurement of the parameters at different voltage and switch conditions is illustrated by the following tabulation:

| Switch 1 | Switch 2 | Measured Parameter |
|---|---|---|
| open | closed | open circuit potential |
| closed | open | closed circuit current |

It will be noted that the applied potential from the power supply 51 may be varied so as to measure externally driven current flow or self driven current flow, in which case the driving potential will be provided by the electrode reaction itself.

It will further be understood that with both switch 1 and switch 2 closed one measures both an applied potential and a derived current whose values relate to concentrations of dissolved gases or ionic species, and further that the number of measurements required corresponds to the number of unknowns to be determined.

It is found that the active metal sensor area of the cathode 31 is advantageously self-renewing so that it continually presents a clean metal surface by a natural flaking off of the metal oxide layer. Therefore it has excellent polarographic properties for catalyzing the transfer of electrons from the tip thereby causing reliably reproducable ionization of the dissolved molecular analyte. The magnitude of the active surface area of the electrode is not critical and is subject to variation. However, it turns out that in the polarographic mode a relatively small surface area is preferred for faster reactivity. A sensor tip with layered base metal/metal oxide other than antimony/antimony oxide can be used. Such materials include bismuth/bismuth oxide or tantalum/tantalum oxide.

Figure 3:
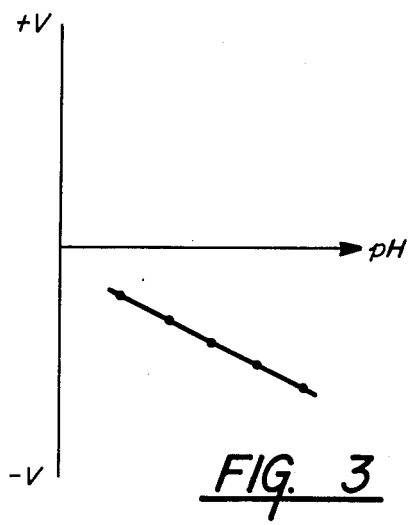
FIGS. 3 and 4 are plots illustrating respectively the pH sensitivity expressed as output voltage and negative current flow/oxygen concentration characteristics of the active polarographic electrode apparatus, in a preferred embodiment according to the invention.
Figure 4:
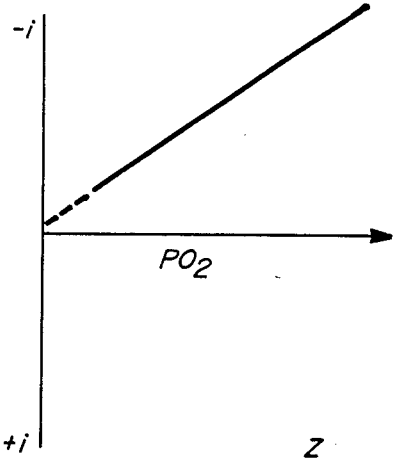
Figure 2:
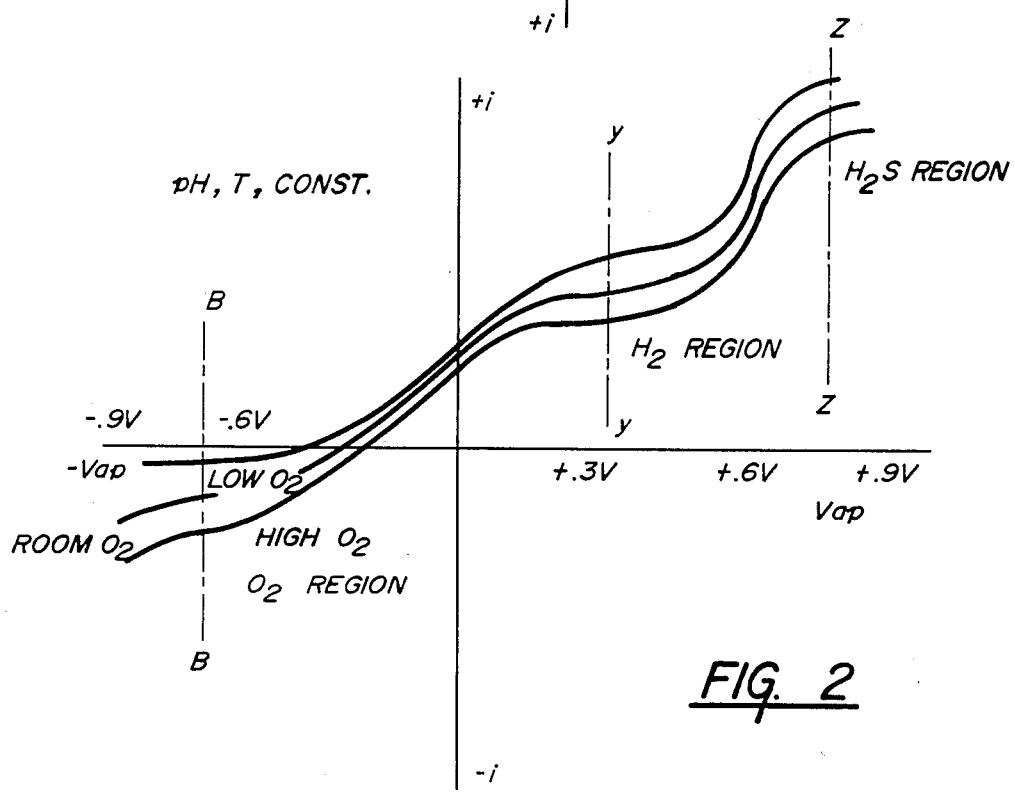
FIG. 2 illustrates schematic $PO_2$, $PH_2$ and $P(H_2S)$ polarograms obtained at constant pH and temperature with preferred sensor apparatus and methods according to the invention.

Referring to FIG. 2, the measurement of dissolved oxygen, $PO_2$, in an aqueous sample, according to a preferred embodiment of the invention can be done by measuring the open circuit potential which measurement correlates (FIG. 3) with the sample pH and by also measuring the current flow due to either a negative applied driving potential lying centrally (line B—B) on the oxygen plateau region $P_1$, or by utilizing the self potential of the couple formed by the electrode and its reference. By operating the system on the plateau, interfering effects due to pH change are neglible. The oxygen concentration relative to current flow, as illustrated in FIG. 4, is given by the observed current flow corresponding, by comparison with reference standards, to the appropriate $PO_2$ curve selected from the family of plateau curves in the $P_1$ region. (FIG. 2 is not drawn to scale and is for illustrative purposes only.)

In similar fashion, the measurement of dissolved gas concentration for a gas other than oxygen can be done. Thus, the measurement of dissolved hydrogen, $PH_2$, or hydrogen sulfide $P(H_2S)$, respectively, can be done by measurement of the closed circuit current using a positive driving potential (line Y—Y or line Z—Z) corresponding to the family of plateau curves in the $P_2$ region or the $P_3$ region of FIG. 2. In each instance, measurements of open circuit potential and current flow may be used in comparison with calibrated reference standards which dictate which plateau of the family of plateau curves is the appropriate measure of the true gas concentration.

The configuration of the gas sensor electrode apparatus of the invention and its application can take any of various forms. For example, it can be in the form of an open chamber or an enclosed chamber which may be a flowthrough chamber adapted to exclude extraneous gas components. Also, it may take the form of an intracorporeal (e.g., intravascular, periodontal, subgingival, etc.) probe having a microelectrode sensor tip.

What is desired to claim as my exclusive property in the invention, is the following:

1. The electrochemical method of simultaneously or sequentially measuring in a liquid both a dissolved ionic species and a dissolved gas including the steps of:
    (a) providing a single polarographically active working electrode having an electrochemically active, base metal/metal oxide surface having the property of providing a stable electrochemical potential that is a quantitative measure of said ionic species and acting as a catalyst for electron transfer allowing for a quantitative polarographic or amperometric measure of said dissolved gas;
    (b) providing a reference electrode;
    (c) measuring the open circuit voltage generated by the electrode pair;
    (d) measuring the closed circuit current flow either in driven mode or in self-generated mode, and comparing said voltage and current values with predetermined voltage and current reference standards to provide multiple values of parameters representative of concentrations of said ionic species and dissolved gas.

2. The method according to claim 1 where the working electrode is a self-renewing base metal electrode.

3. The method according to claim 1 where the working electrode is an antimony/antimony oxide electrode.

4. The method according to claim 2 where the reference electrode is a silver/silver chloride electrode or calomel electrode.

5. The method according to claim 1 where the current flow measured is that of the short circuit current flow.

6. The method according to claim 1 where the concentration of dissolved oxygen is measured.

7. The method according to claim 1 where the concentration of dissolved hydrogen is measured.

8. The method according to claim 1 where the concentration of dissolved hydrogen sulfide is measured.

9. The method according to claim 1 where the hydrogen ion concentration is measured.

10. The electrochemical method of measuring the concentration of an ionizable analyte and two dissolved gaseous analytes contained in an aqueous solution, comprising the steps of:
  (a) providing a base metal/metal oxide working electrode which is polarographically active in the presence of the gaseous analytes;
  (b) providing a reference electrode;
  (c) carrying out first and second measurements of the polarographic current at given first and second applied steady-state voltages, respectively, and comparing the resulting observed first and second current values with predetermined reference standards to provide two values representative of the concentrations of two gas analytes of interest; and,
  (d) measuring the open circuit voltage, said voltage correlatable with the concentration of the ionizable analyte.

11. The method according to claim 10 where the working electrode is a self-renewing base metal electrode.

12. The method according to claim 10 where the working electrode is an antimony/antimony oxide electrode.

13. The method according to claim 11 where the reference electrode is a silver/silver chloride electrode or calomel electrode.

14. The method according to claim 10 where the concentration of oxygen is measured.

15. The method according to claim 10 where the concentration of dissolved hydrogen is measured.

16. The method according to claim 10 where the concentration of hydrogen sulfide is measured.

* * * * *